(12) United States Patent
Jho et al.

(10) Patent No.: US 9,884,150 B2
(45) Date of Patent: Feb. 6, 2018

(54) SYSTEMS AND METHODS FOR IDENTIFYING AND LOCATING AN IMPLANTED DEVICE

(75) Inventors: Jiaye Z. Jho, Salt Lake City, UT (US); Jeremy B. Cox, Salt Lake City, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 709 days.

(21) Appl. No.: 13/101,968

(22) Filed: May 5, 2011

(65) Prior Publication Data

US 2011/0275930 A1 Nov. 10, 2011

Related U.S. Application Data

(60) Provisional application No. 61/331,779, filed on May 5, 2010.

(51) Int. Cl.
*A61M 5/142* (2006.01)
*A61B 5/06* (2006.01)
(Continued)

(52) U.S. Cl.
CPC ......... *A61M 5/14276* (2013.01); *A61B 5/064* (2013.01); *A61B 8/0841* (2013.01); *A61B 2562/08* (2013.01); *A61M 2039/0238* (2013.01)

(58) Field of Classification Search
CPC ....... A61B 8/00; A61B 5/055; A61B 2562/08; A61B 5/064
(Continued)

(56) References Cited

U.S. PATENT DOCUMENTS 5,423,334 A    6/1995   Jordan
5,771,895 A * 6/1998   Slager ......................... 600/462
(Continued)

FOREIGN PATENT DOCUMENTS

CN    103327902 A    9/2013
JP     H6-296633 A    10/1994
(Continued)

OTHER PUBLICATIONS

PCT/US2011/035406 filed May 5, 2011 International Seach Report dated Dec. 16, 2011.
(Continued)

*Primary Examiner* — Rochelle Turchen
(74) *Attorney, Agent, or Firm* — Rutan & Tucker, LLP

(57) ABSTRACT

A system for identifying an attribute of an implanted medical device, such as an access port is disclosed. In one embodiment, the identification system comprises a marker included with the implanted medical device, wherein the marker relates to an attribute of the implanted medical device. An external detection device is also included, comprising a signal source that emits an incident electromagnetic signal for impingement on the marker of the implanted medical device, a detector that detects a return signal from the marker resulting from impingement of the incident electromagnetic signal, and a user interface for conveying information relating to the attribute based on detection of the return signal. In the case of an implantable access port, for instance, the described system enables information, such as the ability of the port to withstand power injection of fluids therethrough, to be ascertained even after the port has been subcutaneously implanted within the patient.

14 Claims, 10 Drawing Sheets

(51) Int. Cl.
*A61B 8/08* (2006.01)
*A61M 39/02* (2006.01)

(58) Field of Classification Search
USPC .............................. 600/437, 459, 462, 466
See application file for complete search history.

(56) References Cited

U.S. PATENT DOCUMENTS

| | | | |
|---|---|---|---|
| 6,654,629 B2* | 11/2003 | Montegrande | 600/424 |
| 2002/0067359 A1* | 6/2002 | Brodsky et al. | 345/440 |
| 2003/0204165 A1 | 10/2003 | Houben et al. | |
| 2005/0059884 A1 | 3/2005 | Krag | |
| 2006/0264898 A1* | 11/2006 | Beasley et al. | 604/506 |
| 2008/0021313 A1 | 1/2008 | Eidenschink et al. | |
| 2009/0227951 A1 | 9/2009 | Powers et al. | |
| 2010/0010339 A1 | 1/2010 | Smith et al. | |
| 2010/0298704 A1* | 11/2010 | Pelissier et al. | 600/443 |

FOREIGN PATENT DOCUMENTS

| | | |
|---|---|---|
| JP | 2004-283289 A | 10/2004 |
| JP | 2006-102360 A | 4/2006 |
| JP | 2008-539025 A | 11/2008 |
| JP | 2013-531999 | 8/2013 |
| WO | 2006116438 A2 | 11/2006 |
| WO | 2011140379 A2 | 11/2011 |

OTHER PUBLICATIONS

PCT/US2011/035406 filed May 5, 2011 Written Opinion dated Dec. 16, 2011.
MX/a/2012/012802 filed Nov. 1, 2012 Office Action dated May 31, 2013.
MX/a/2012/012802 filed Nov. 1, 2012 Office Action dated Nov. 19, 2013.
JP 2015-249575 filed Dec. 22, 2015 Decision for Rejection dated May 22, 2017.
JP 2015-249575 filed Dec. 22, 2015 First Office Action dated Oct. 4, 2016.
CN 201180033387.5 filed Jan. 5, 2013 First Office Action dated Oct. 16, 2014.
CN 201180033387.5 filed Jan. 5, 2013 Second Office Action dated Apr. 13, 2015.
CN 201180033387.5 filed Jan. 5, 2013 Third Office Action dated Sep. 2, 2015.
JP 2013-509275 filed Oct. 30, 2012 Decision of Rejection dated Sep. 2, 2015.
JP 2013-509275 filed Oct. 30, 2012 First Office Action dated Feb. 6, 2015.
PCT/US2011/035406 filed May 5, 2011 International Preliminary Report on Patentability dated Feb. 20, 2014.

* cited by examiner

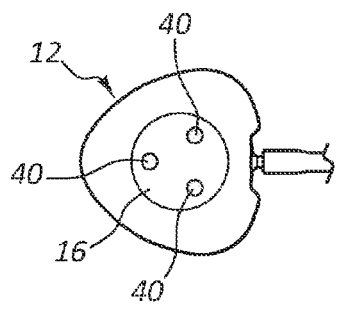 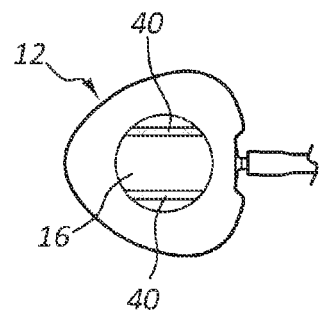 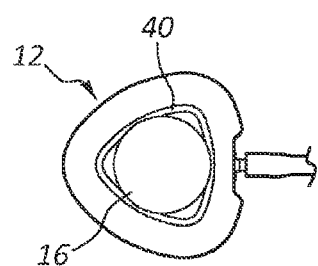
FIG. 10A  FIG. 10B  FIG. 10C
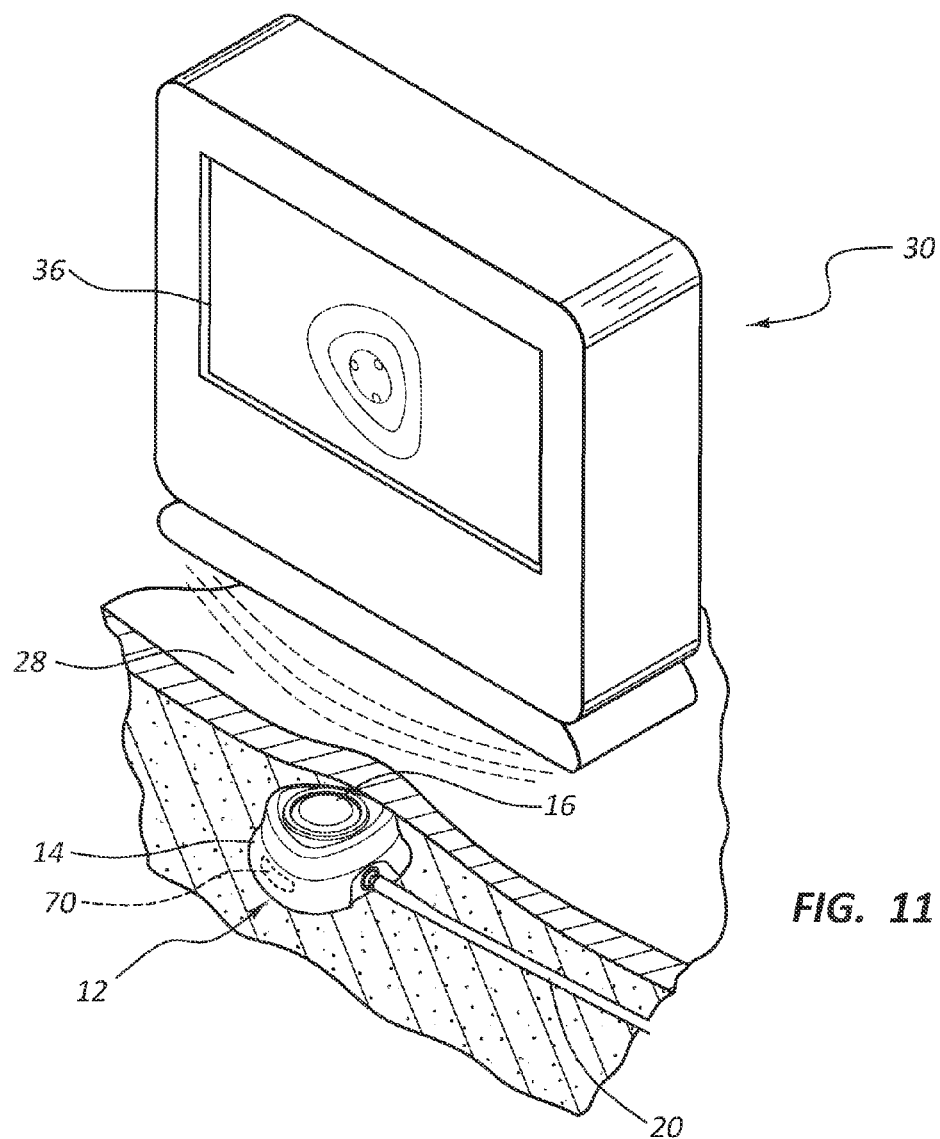
FIG. 11

SYSTEMS AND METHODS FOR IDENTIFYING AND LOCATING AN IMPLANTED DEVICE

CROSS-REFERENCE TO RELATED APPLICATIONS

This application claims the benefit of U.S. Provisional Patent Application No. 61/331,779, filed May 5, 2010, and entitled "Systems and Methods for Identifying and Accessing an Implanted Device," which is incorporated herein by reference in its entirety.

BRIEF SUMMARY

Briefly summarized, embodiments of the present invention are directed to a system for identifying an attribute of an implanted medical device, such as an access port. Information about the device, such as type, size, location, power injectability, etc. can be ascertained, thus increasing device success, user convenience, and patient safety.

In one embodiment, the identification system comprises a marker included with the implanted medical device, wherein the marker relates to an attribute of the implanted medical device. An external detection device is also included for externally detecting the implanted device. The detection device includes a signal source that emits an incident electromagnetic signal for impingement on the marker of the implanted medical device, a detector that detects a return signal from the marker resulting from impingement of the incident electromagnetic signal, and a user interface for conveying information relating to the attribute based on detection of the return signal. In the case of an implantable access port, for instance, the described system enables information, such as the ability of the port to withstand power injection of fluids therethrough, to be ascertained after the port has been subcutaneously implanted within the patient.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 10A-10C show various examples of markers for an access port according to one embodiment;

FIG. 11 is a partial cross sectional perspective view of an implanted access port and identification system according to one embodiment;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to a system for identifying and/or locating an implanted medical device, such as an access port, and for facilitating access to such a device. In particular, identification of an attribute of the medical device after implantation enables a clinician to better utilize the device, thus increasing device success, user convenience, and patient safety. In addition, and as mentioned, the system can assist in locating and accessing the implanted device, such accessing an access port with a needle, for instance.

It is appreciated that, though use of the systems and components described herein focuses on identification of and access to an implanted access port, other types of implanted devices, including medical devices, can benefit from the principles and embodiments described herein.

Figure 1:
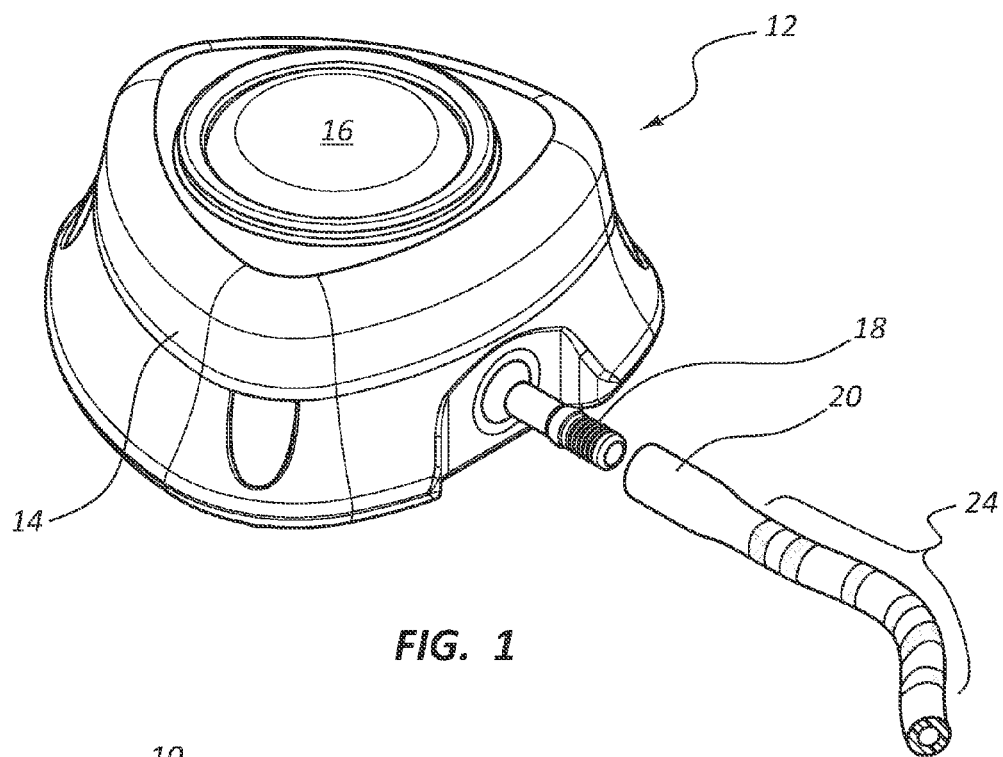
FIG. 1 is a perspective view of an access port and catheter including a plurality of markers, according to one embodiment.
Figure 2:
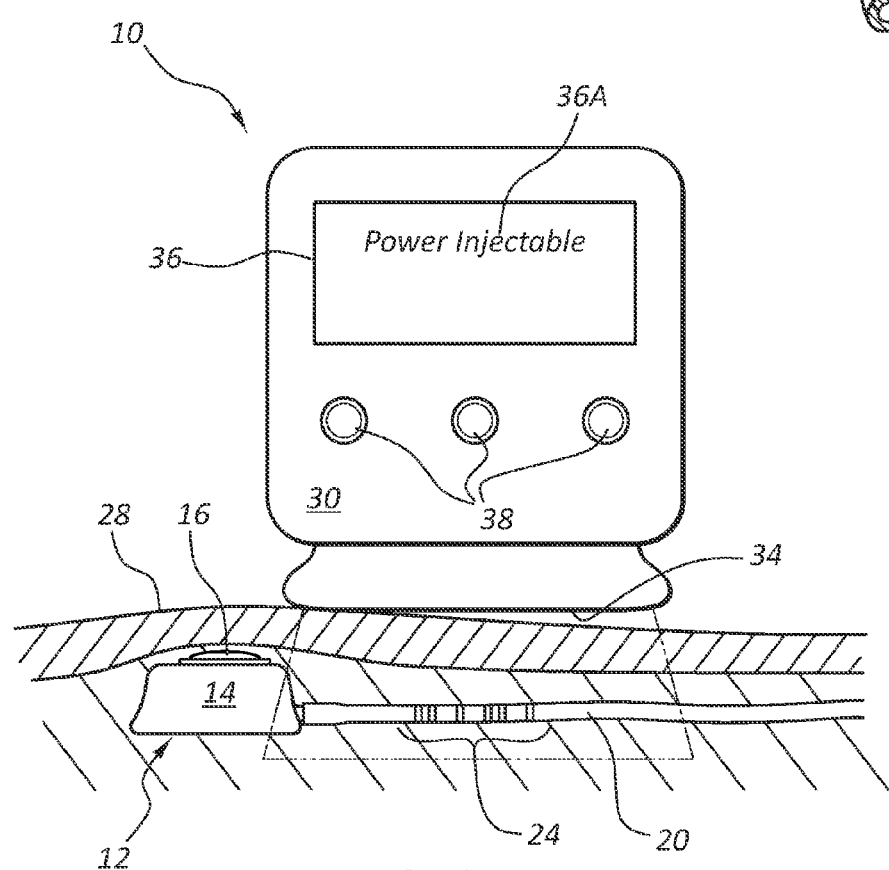
FIG. 2 is a partial cross sectional side view of an implanted access port and identification system according to one embodiment.

Reference is first made to FIGS. 1 and 2, which depict various details of an implantable access port 20 and a related system, generally designated at 10, for identifying and/or characterizing the access port or other implanted medical device, according to one embodiment. As shown, the access port 20 includes a body 14 defining a fluid cavity that is covered by a septum 16. A stem 18 extends from the port body 14 and serves as an outlet for the fluid cavity. As shown in FIG. 2, the stem 18 is configured to operably connect to a catheter 20 so as to provide fluid communication between the catheter and the port fluid cavity. Note that the catheter 20 is merely representative of a wide variety of catheters, including PICCs, central catheters, etc., which can be employed. Also, though described herein primarily as an access port, the medical device of the embodiments discussed herein can optionally include any number of devices subcutaneously implantable into a body of a patient. The embodiments to be described should therefore not be so limited.

In accordance with one embodiment, one or more markers 24 are included on a portion of the catheter 20 as part of the identification system 10. Each marker 24 is configured so as to be visible when imaged by an ultrasound device after implantation of the access port 12 under the skin 28 of the patient (FIG. 2). As shown in FIGS. 1 and 2, the markers 24 can be arranged in a specified pattern, such as a "barcode" format, that can provide information regarding one or more attributes of the access port to which the catheter 20 is operably connected, as in FIG. 2. For instance, the markers 24 can relate in one embodiment to the ability of the access port to withstand a relatively high fluid flow rate therethrough, also referred to herein as "power injection." In one embodiment, for instance, power injection fluid flow rates include a flow of about 5 ml per second at a pressure of about 300 p.s.i., though other flow rates and pressures are also possible. In addition, other attributes of the access port and/or catheter or other medical device can also be indicated by the markers 24, including port size, type, fluid cavity capacity, date of implantation, etc.

In one embodiment, the markers 24 include a material that varies in density and/or surface reflectivity from the catheter material so as to provide an ultrasonically detectable specimen. In another embodiment, the markers 24 include an ultrasonically opaque, non-metallic and MRI-compatible dye included in a translucent catheter, such as by coating the catheter, extruding it into the catheter, etc.

In another embodiment, it is appreciated that the markers can be configured to be imaged or detected via another modality that is sufficiently transmissive through body tissue including optical, RF, fluorescence (such as via UV or IR-wavelength electromagnetic radiation), magnetic, etc. In one embodiment, for example, the markers can include a dark material such as tungsten, to provide a high dark/light contract between the markers and the catheter, port, etc., such that the contrast is detected when illuminated by a suitable light source and optically imaged by a camera. Also, the markers in one embodiment can be included on the body of the access port itself.

The system 10 further includes a detection device, or external identification ("ID") device 30, configured to detect the markers 24 of the implanted catheter 20 (or, optionally, the port 12) when the device is brought into sufficient proximity to the subcutaneous markers 24 while remaining external to the patient's body, such as by placing the ID device against the patient's skin 28. In the present embodiment the ID device 30 includes an ultrasound imaging device. As such, the ID device 30 includes an imaging head 34 housing a transducer for emitting ultrasound signals and detecting reflected signals. Note that the markers 24 in one embodiment are sufficiently spaced apart from one another to enable the transducer to discern each of the markers according to the resolution of the transducer.

In particular, the ultrasound signal emitted by the transducer of the imaging head 34 is configured to travel through the patient's body tissue and impinge on the markers 24 of the catheter 20. The ultrasound signal is then reflected and, as a return signal, is detected upon receipt by the transducer. The ID device 30 includes the circuitry and algorithms to enable the return signal to be processed and for information relating to detection of the markers 40 to be conveyed to a user via a user interface, such as a display 36 included on the ID device.

For instance, in the embodiment shown in FIG. 2, the display 36 includes a image 36A including a message, "power injectable," to indicate that the access port to which the catheter 20 including the markers 24 is connected is capable of withstanding the pressures and fluid flow rates associated with power injection. In the case of the markers 40 forming a detectable pattern, barcode, etc., the ID device circuitry and algorithms can include functionality to enable the detected pattern to be interpreted so as to enable identification of the attribute indicated by the markers 24 to be conveyed to the user of the ID device 30 via the user interface. In another embodiment, the ID device merely conveys the presence, number, shape, or other configuration of the markers themselves so that a user can interpret the markers and determine the attribute represented thereby.

It is appreciated that other messages and/or identifying information can be depicted on the display 36 relating to the attribute of the access port or other implanted medical device about which the one or more markers 24 are concerned. In other embodiments, it is also appreciated that other user interface modalities can be employed, including audio elements, lights, etc., to convey to a user of the ID device information relating to the detected markers. One or more control buttons 38 or other control interfaces are included to control functionality of the ID device 30.

Figure 3A:
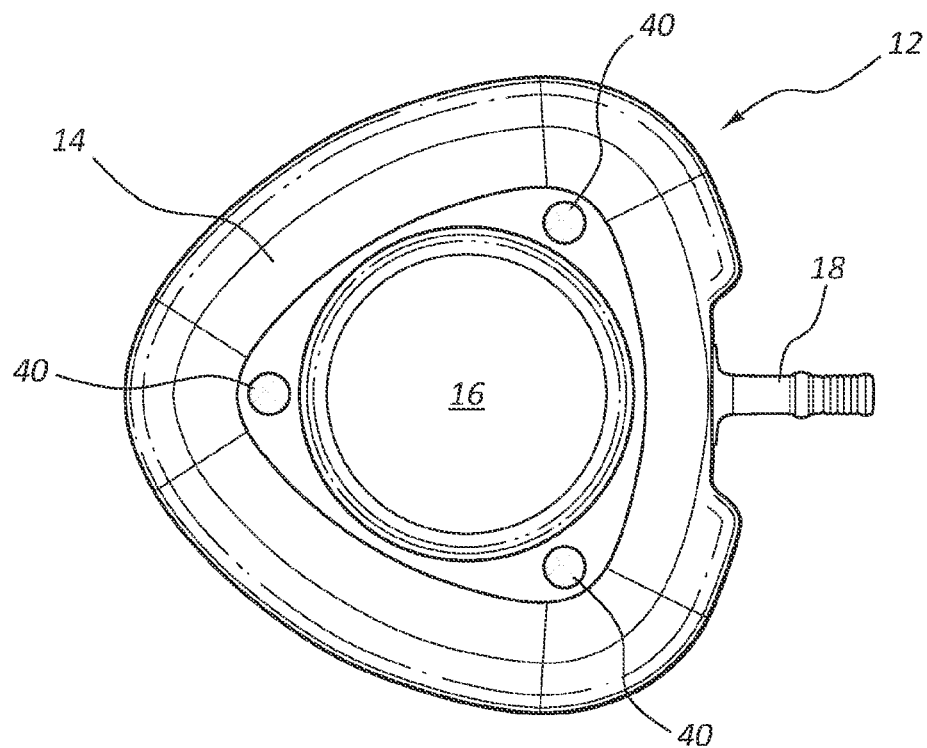
FIG. 3A is a top view of an access port including a plurality of markers according to one embodiment.
Figure 3B:
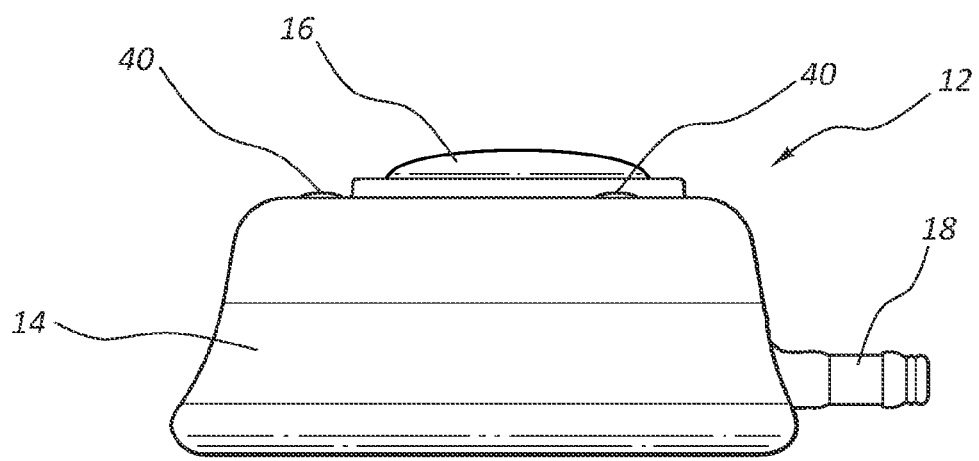
FIG. 3B is a side view of the access port of FIG. 3A.

As mentioned above, the markers of the access port or other implanted medical device can include other modalities instead of ultrasound. FIGS. 3A and 3B depict one example of this, wherein the access port 12 includes a plurality of markers 40 that are configured to react to impingement thereon of electromagnetic radiation of a predetermined wavelength. In particular, three markers 40 are positioned on the body 14 of the access port in a triangular configuration about the septum 16. Other numbers, sizes, positions, etc., of the markers can also be employed with this or other types of implantable medical devices. The markers 40 can be attached to or integrated with the port body 14 in any number of suitable ways, including deposition or adhesion of a marker material on the port surface, molding or insertion into a cavity defined in the port, etc. In one embodiment, all or a portion of the access port body itself can serve as a marker, wherein the body material includes material that enables it to produce a return signal as further described below.

When disposed on an access port or other device that is implanted within the patient's body, the markers 40 described above are configured to emit, reflect, or fluoresce a return beam of electromagnetic radiation when impinged by an incident, external beam of electromagnetic radiation directed through the patient's skin and tissue toward the implanted port. For instance, in one embodiment, the markers 40 on the implanted port 12 include a material that emits a return beam of radiation of infrared wavelength when impinged upon by an incident beam of infrared electromagnetic radiation. The emitted infrared radiation from the markers 40 can be detected external to the patient, thus enabling information regarding one or more attributes of the port to be ascertained after port implantation.

In another embodiment, other wavelengths of electromagnetic radiation can form the incident beam, such as radiation in the ultraviolet ("UV") wavelength, resulting in a return beam of UV radiation from the markers 40 and through the patient's tissue for detection outside of the patient's body.

Note that the term "beam" is used herein merely to indicate some amount of radiation travelling in one or more general directions. In yet other embodiments, other suitable radiation wavelengths, including visible or radiofrequency ("rF") wavelengths may be employed. Also, in one embodiment, the markers can be configured such that, when impinged by an incident beam of radiation of a first wavelength, they emit a return beam of radiation of a second, distinct wavelength, such as IR for the incident beam and UV for the return beam. In this instance, an organic IR-to-UV photo-excitable phosphor with suitable fluorescence can be employed for the marker. Such a marker may need to be encapsulated so as to provide biocompatibility. More generally, other suitable phosphors may be employed in the described embodiments. In another embodiment, the radiation emitter can simultaneously or sequentially emit radiation over a spectrum of wavelengths and the return beam includes one or more of the wavelengths emitted. In yet another embodiment, the marker can include an LED light attached to or integrated with the medical device, the LED light being detectable by an external detection device when the illuminating. These and other such variations are therefore contemplated.

Figure 4A:
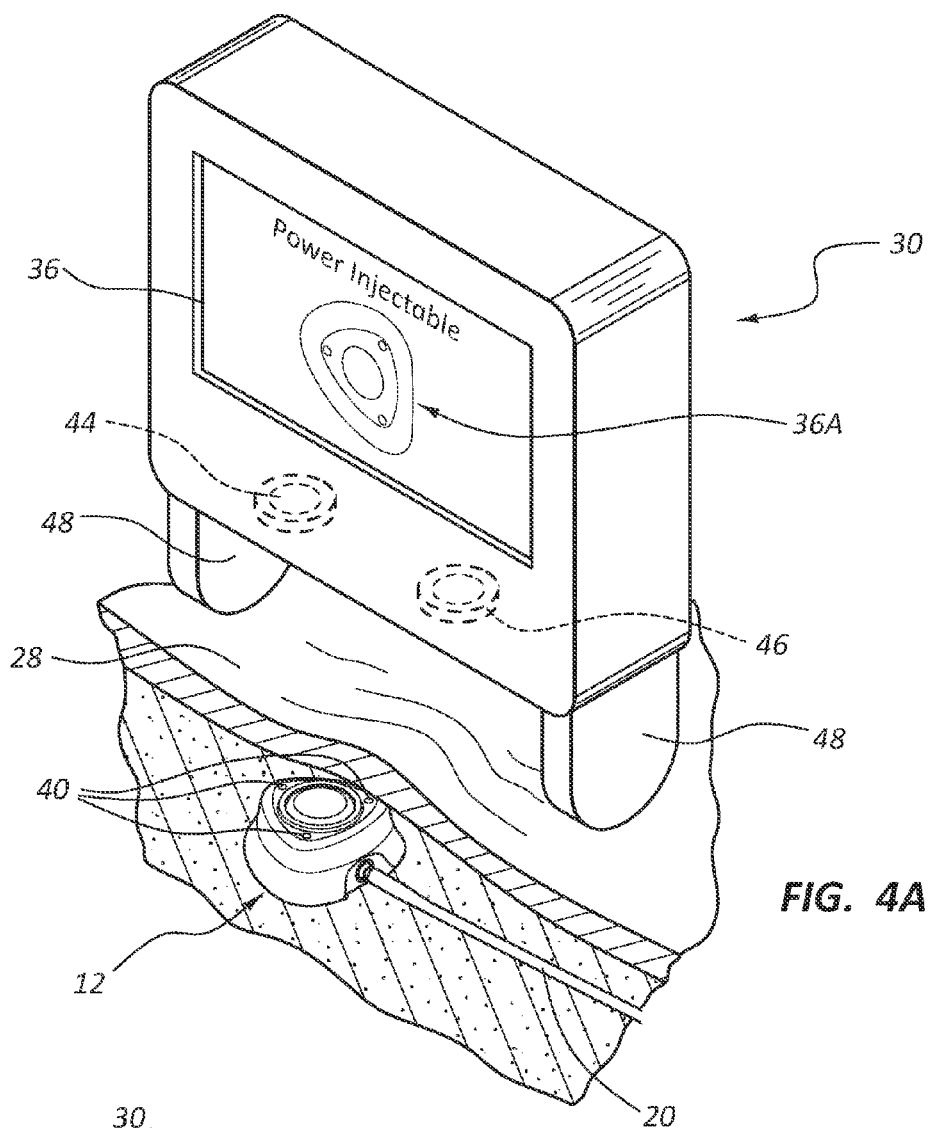
FIG. 4A is a partial cross sectional perspective view of an implanted access port and identification system according to one embodiment.
Figure 4B:
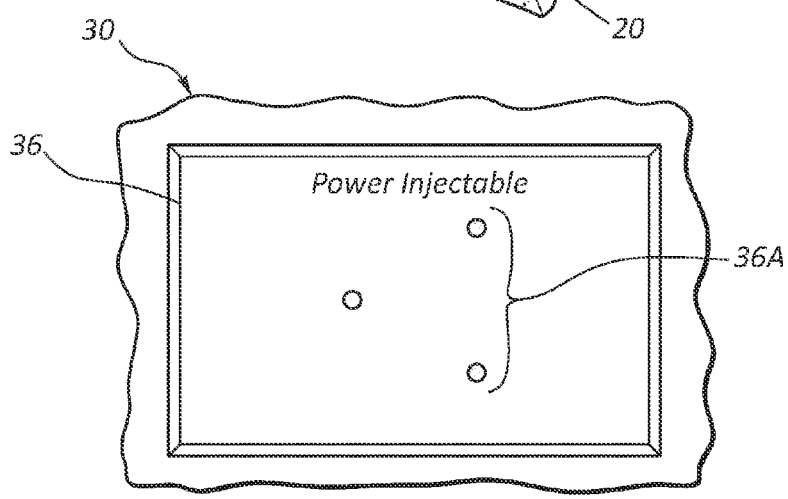
FIG. 4B is a side view of a display portion of the identification device shown in FIG. 4A.

FIGS. 4A and 4B show details of the ID device 30, configured here to detect an implanted port, such as the port 12 including the markers 40 as shown in FIGS. 3A and 3B, post-implantation. As shown, the ID device 30 in the present embodiment includes a signal source, such as an LED 44, for producing and emitting the incident beam of infrared electromagnetic radiation. The ID device 30 further includes a detector, such as a CCD camera 46, for detecting a return beam of radiation received from the markers 40. The LED 44 and camera 46 are disposed on a bottom face of the ID device 30 or in another manner to provide for suitable transmission and reception of the radiation beams. Standoffs 48 are included with the ID device 30 in the present embodiment to provide for adequate separation of the LED and camera with respect to the patient's skin 28 and the implanted port 12. In other embodiments, the standoffs can be adjustable or omitted from the ID device. In yet another embodiment, the beam produced by the LED or other signal source can be focused.

As shown in FIG. 4A, during operation the ID device is placed against the skin 28 of the patient proximate the location where the port is believed to be subcutaneously disposed. In the present embodiment, the standoffs 48 of the ID device 30 are placed into contact with the skin 28, but in other embodiments, the ID device can be merely held over the skin without contacting it. An incident beam of infrared radiation is emitted by the LED 44 and directed for travel through the body tissue for impingement upon the markers 40 included on the subcutaneous port 12. Impingement of the incident beam on the markers 40 causes the markers to emit a return beam of infrared radiation that is transmitted through the body tissue and detected by the camera 46 of the ID device 30. As before, the ID device 30 includes suitable circuitry and algorithms to interpret the return beam and determine the attribute(s) of the port 12 as indicated by the markers 40, such as the power injectability of the port, for instance.

In one embodiment, for example, detection by the ID device 30 of the return beam of infrared radiation indicates that an implanted device including markers that produced the return beam is located below the device. The ID device 30 can then interpret the received return beam according to data programmed, stored, or otherwise received by the device as to the attribute represented by the marker of the port that produced the return beam. Information relating to the port attribute can then be depicted on the display 36 of the ID device 30, or otherwise conveyed to the user of the ID device. FIG. 4A gives one example of an image 36A depicted on the display 36, providing a stored representative image of the port and indicating that the port is power injectable. FIG. 4B gives another example of the image 36A, wherein depictions of the markers 40 as detected according to the present position of the ID device 30 over the access port 12 are shown together with an indication of the power injectability of the port. It is therefore appreciated that a wide variety of depictions can be displayed by the system 10 to indicate a wide variety of attributes of the access port or other implanted medical device. In one embodiment, it is appreciated that the ID device can be used to identify different types of devices, e.g., access ports vs. catheters, etc.

With respect to the incident beam of electromagnetic radiation, it is appreciated that the wavelength thereof can be tuned by the ID device so as to more readily enable identification of the return beam from the port markers when received by the device and prevent possible confusion by other proximate radiation sources that may be present. Also note that the markers can be configured to emit a return beam of wavelength different than that of the incident beam, as already mentioned. These and other such variations are therefore contemplated.

Figure 5:
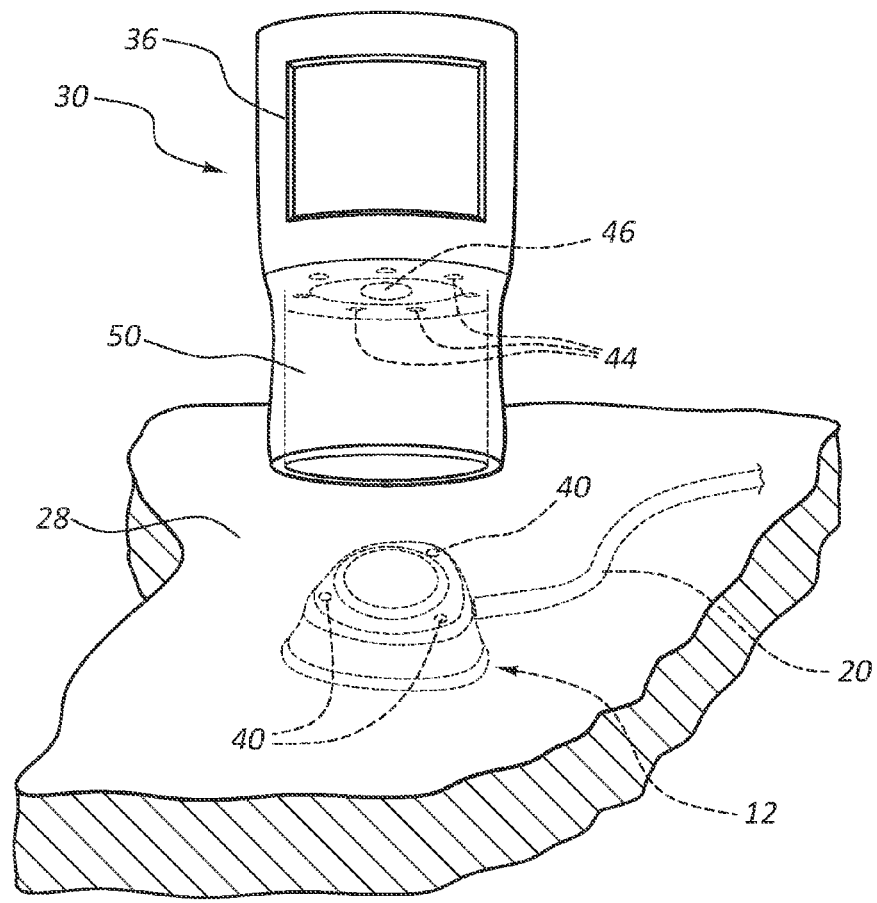
FIG. 5 is a perspective view of an identification device including a light shield according to one embodiment.
Figure 6:
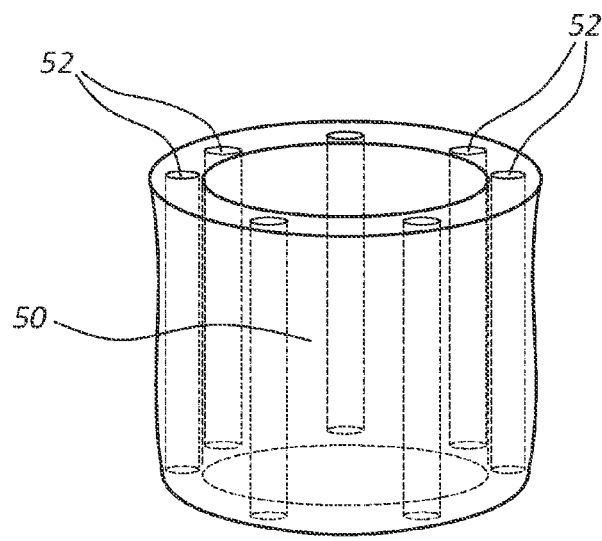
FIG. 6 is a perspective view of the light shield of FIG. 5.

FIGS. 5 and 6 show various details regarding the ID device 30 according to one embodiment, wherein a light shield 50 including opposing open ends is included for attachment to a bottom portion of the device. So configured, the light shield 50 can act as a shield to prevent environmental light or other electromagnetic radiation from entering the volume within the tube, thus enabling the camera 46, disposed within the dark are created by the light shield, to be a low-lux camera. In such an embodiment, the light shield 50 is manufactured as to be substantially non-transmissive to electromagnetic radiation that would interfere with the sensitivity of the camera 46. Such non-transmissiveness can be achieved via a coating applied to the outer or inner shield surface, or by including non-transmissive materials in the material from which the light shield is formed.

As shown in FIG. 5, in one embodiment a plurality of LEDs 44 can be arranged about a bottom perimeter of the ID device 30 such that beams emitted from each LED are transferred to the tissue of the patient primarily along beam paths 52 through the longitudinal length of the light shield 50 itself when attached to the ID device. The light shield 50 can include acrylic or other suitable material, and can be removably or permanently attached to the ID device 30. Though cylindrical here, the light shield can include one of several possible shapes to accommodate mating with the ID device and the patient's skin surface.

Figure 7:
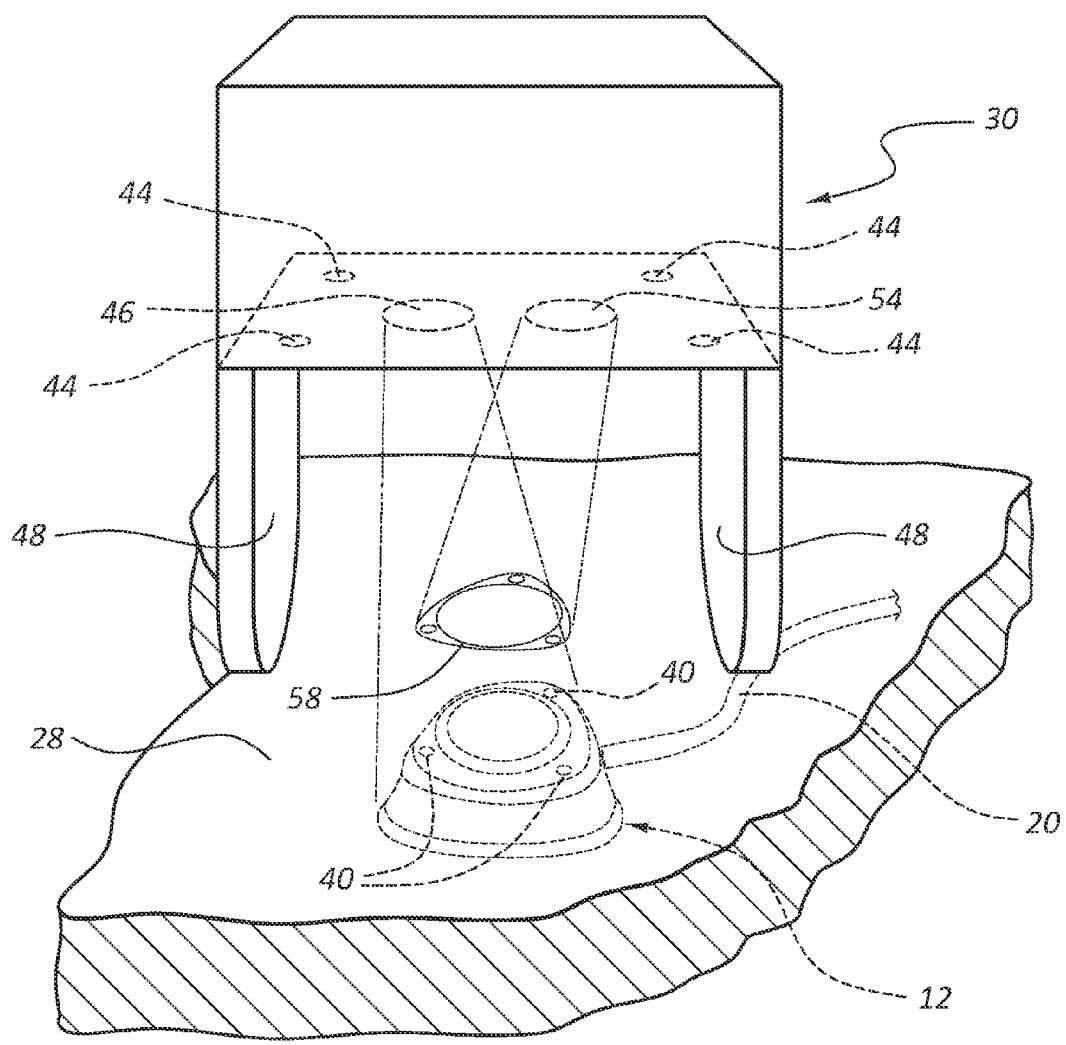
FIG. 7 is a perspective view of an identification device according to one embodiment.

FIG. 7 shows another embodiment of the ID device 30, wherein a projector 54 is included on a bottom face of the device so as to enable a representative projection of the detected access port 12 or other implanted device to be displayed on the skin 28 of the patient directly above the detected location of the port. In particular, detection of the access port 12 is made via the use of an incident beam (produced by the LEDs 44 of the ID device 30) impinging on the markers 40 of the port 12 and consequent reception of a return beam from the markers 40 as detected by the camera 46, as in earlier embodiments. This in turn enables an attribute of the port 12, i.e., its location under the skin 28, to be determined by the ID device 30, due to the ability of the ID device to determine the geometries of the incident beam, the return beam, and the projected image path. Once the port location is determined, the ID device 30 can project a representative projected image 58 of the access port, the markers, etc., on to the skin 28 above the implanted port location, via the projector 54. This enables a clinician viewing the projected image 58 to ascertain the location of the access port 12 and to conveniently access the septum 16 thereof (FIG. 1) with a needle or other device. Such projection can be employed in addition to or instead of depiction of information on a display of the ID device. The projected image 58 can include one or more of various designs, words, images, etc., including a depiction of the markers actually detected by the camera 46 or an image stored in a memory location of the ID device 30 corresponding to the type of access port identified by the ID device according to the markers detected thereby.

Figure 8:
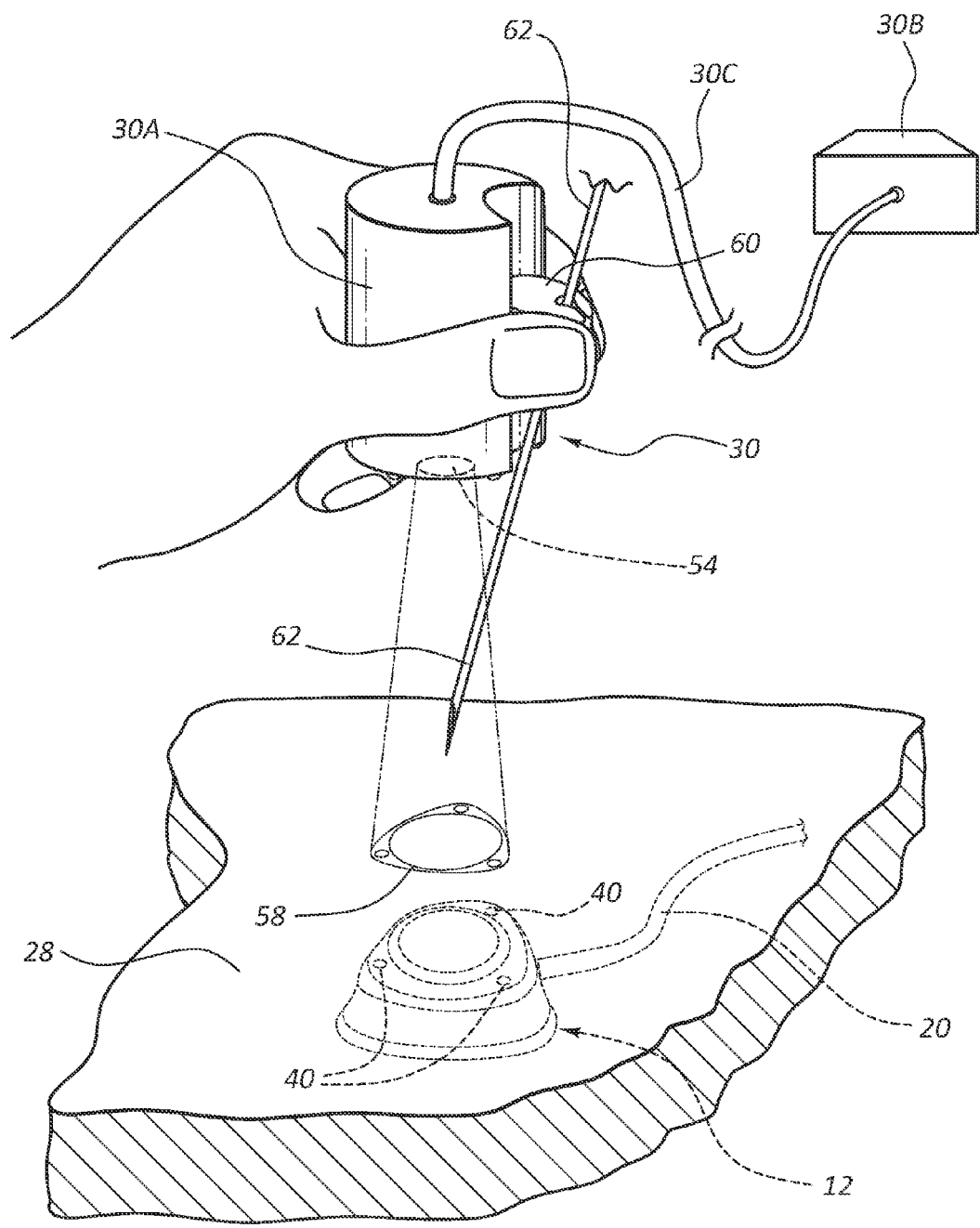
FIG. 8 is a perspective view of an identification device according to one embodiment.

FIG. 8 shows another embodiment of the ID device 30, wherein the ID device 30 is not a self-contained unit, but rather includes separate components. In detail, the ID device 30 includes a handheld module 30A containing a needle guide 60 for holding a needle 62, an outlet for emitting a beam of electromagnetic radiation, a camera for detecting return signals from the markers, and the projector 54 for projecting the image 58 of the port 12, once detected.

The ID device 30 further includes a component module 30B operably connected to the handheld module 30A via a cable 30C. The component module 30B in the present embodiment includes a lighting system for transmitting electromagnetic radiation from the component module to the outlet on the handheld module via a suitable conduit in the able 30C, and necessary circuitry and electronic modules to enable ID device functionality. Such an ID device design provides a relatively small handheld device for use in locating and identifying the implanted device, thus providing enhanced convenience for the user.

Figure 9A:
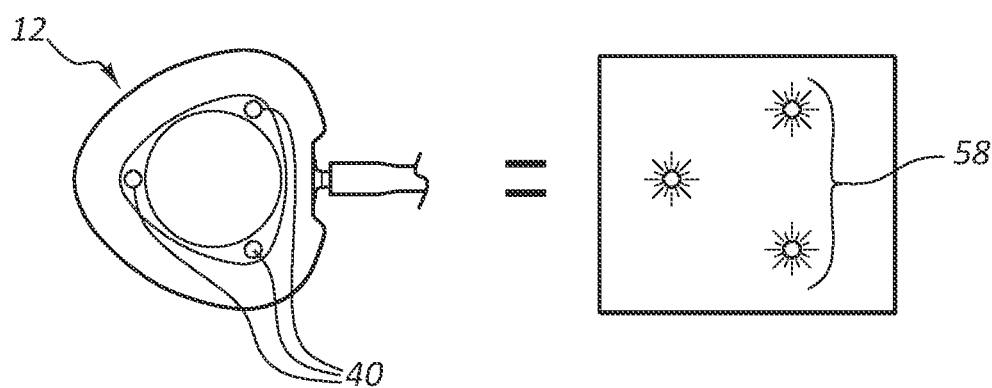
FIGS. 9A and 9B are various views of an access port and representative images as depicted by the identification device according to one embodiment.
Figure 9B:
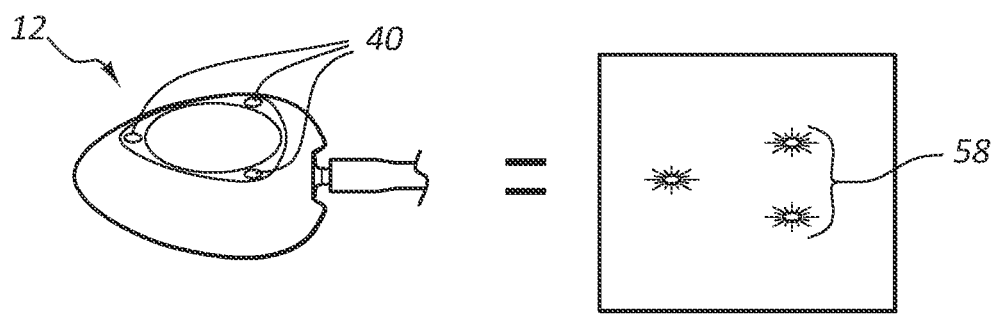

FIGS. 9A and 9B show that a representative image of the implanted access port 12 can assist in determining orientation of the port post-implantation. As shown in FIG. 9A, when the port 12 is positioned within the body so as to be substantially parallel to the skin, the markers 40 thereof will be detected by the ID device with a desired orientation, or spacing, with respect to one another. The ID device projector 54 can then project the representative image 58 of the markers 40 with the same orientation, thus indicating to the observer that the port is properly positioned.

If the port has rotated to an oblique orientation within the body, as seen in FIG. 9B, the ID device 30 will detect the port markers 40 with a different spacing and will display the projected image 58 as such, thus indicating the port orientation is oblique. A similar situation could be observed on the image 36A of the device display 36, if desired (FIGS. 4A, 4B).

FIGS. 10A-10C show examples of other possible configurations for placement of the markers 40 on the access port 12, including placement of marker dots on the port septum 16, stripes across the septum, and a stripe about the septum perimeter. These and other marker configurations are therefore possible, as appreciated by one skilled in the art. Note also that these marker configurations are representative for placement on other implantable devices as well.

FIG. 11 shows that in one embodiment the marker can include an active or passive RFID chip 70, detectable by an RFID reader component included in the ID device 30. So configured, ample information regarding attributes of the access port 12 or other implanted device can be determined upon detection of the RFID chip 70 by the reader of the ID device.

Figure 12A:
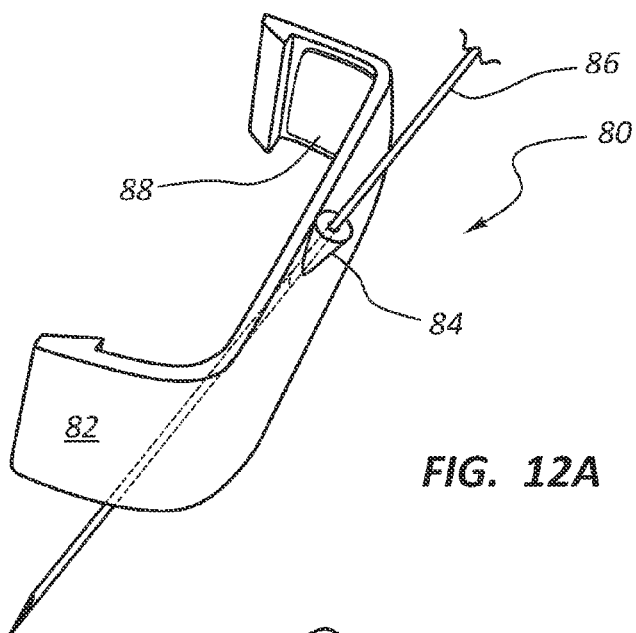
FIGS. 12A-12C show various views of a needle guide and dressing according to one embodiment.
Figure 12B:
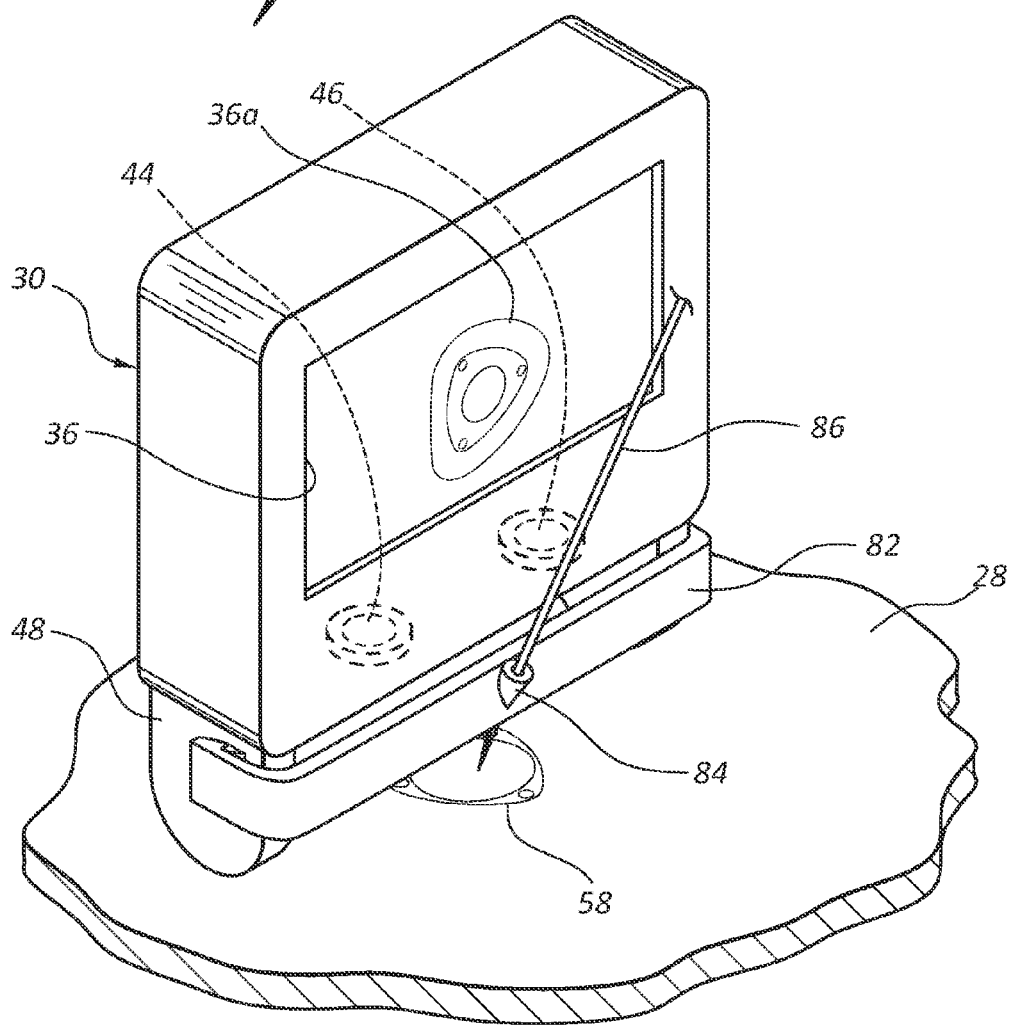
Figure 12C:
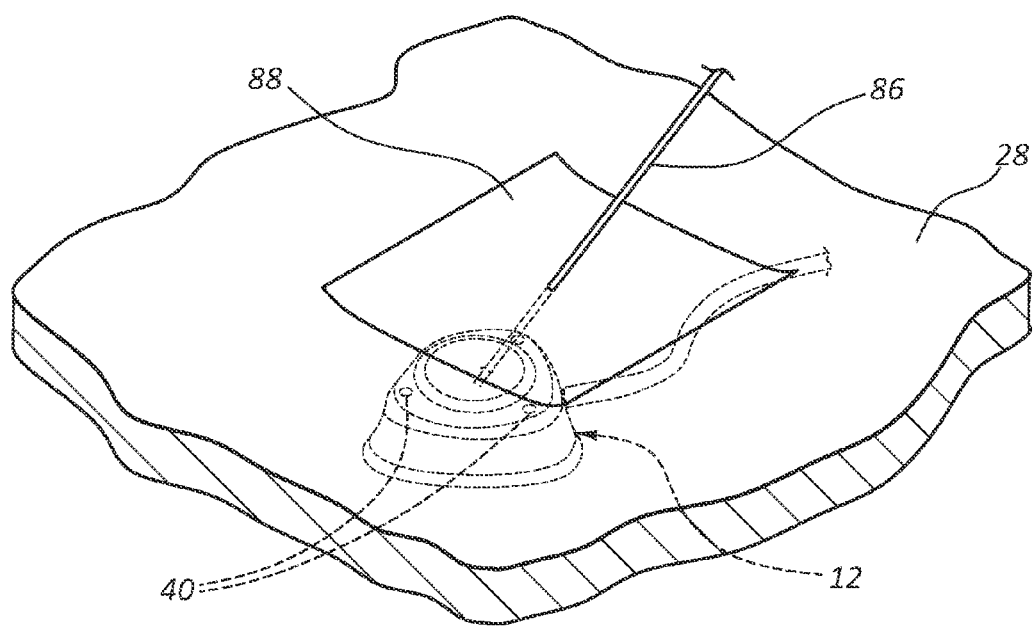

FIGS. 12A and 12B depict details regarding a needle guide assembly 80 for use with the ID device 30, according to one embodiment. The needle guide assembly 80 includes a body 82 configured to snap-on or otherwise attach to a portion of the ID device 30, such as the standoffs 48 (FIG. 12B), when used with an ID device similar to that shown in FIG. 4A. The body 82 includes a needle guide 84 for guiding a needle 86. A dressing 88 is rolled up in an undeployed configuration and attached to a portion of the body 82. The needle 86 pierces both the body 82 and the dressing 88. So configured, the needle guide assembly 80 is useful to guide the needle 86 into the septum of an implanted access port while using the ID device 30 to locate the port, such as via the projected image 58 of the port, as shown in FIG. 12B. After the needle has been placed, the dressing 88 can be removed from the body 82, then unrolled and deployed on the skin over the insertion site of the needle 86 to provide a barrier and dressing for the insertion site, as shown in FIG. 12C. In one embodiment, the dressing includes antimicrobial properties.

Figure 13:
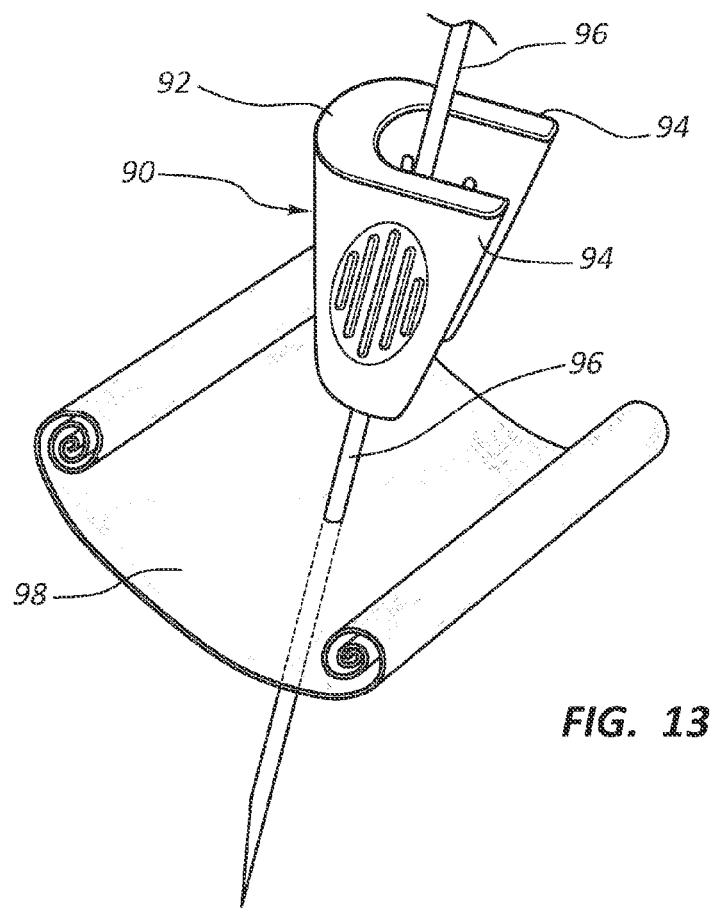
FIG. 13 is a perspective view of a needle guide and dressing according to one embodiment.

FIG. 13 shows a needle guide assembly 90 according to another embodiment, including a body 92 shaped for grasping by a user and a slot defined by the body for receiving therethrough a needle 96. A needle guide can be included in the slot to assist with guiding the needle 96. An undeployed, rolled up dressing 98 (shown partially unrolled in FIG. 13) is also included, the dressing being pre-punctured by the needle 96. The needle guide assembly 90 is employed to enable the needle 96 to be inserted into an insertion site of the patient, then to cover the skin proximate insertion site with the dressing 98 without first removing the needle from the patient.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. An identification system, comprising:
    a catheter and access port in fluid communication, the catheter including a plurality of markers positioned on the catheter detectable via ultrasound when the catheter and the access port are subcutaneously implanted in a patient, the plurality of markers arranged in a predetermined pattern designed to provide information regarding at least one attribute of the access port; and
    a self-contained handheld external detection device, including:
        an ultrasound transducer designed to produce ultrasound signals for impingement on the plurality of markers, and designed to detect ultrasound signal reflection by the markers; and
        a display designed to depict the information regarding the at least one attribute of the access port,
        wherein the detection device is designed to interpret the predetermined pattern to determine the information regarding the at least one attribute of the access port.

2. The identification system as defined in claim 1, further comprising a first marker positioned on a body of the access port.

3. The identification system as defined in claim 2, wherein the plurality of markers are circumferentially positioned on a body of the catheter.

4. The identification system as defined in claim 1, wherein the at least one attribute of the access port includes at least one of: a type or size of the access port, and an ability of the access port to withstand power injection of a fluid.

5. An identification system, comprising:
a catheter and access port in fluid communication, the catheter including a marker positioned on the catheter detectable via ultrasound when the catheter and access port are subcutaneously implanted in a patient, the marker designed to indicate at least one attribute of the access port, the at least one attribute of the access port including an ability to withstand power injection; and
an external detection device, including:
an ultrasound transducer designed to:
produce ultrasound signals for impingement on the marker positioned on the catheter, and
detect ultrasound signal reflection by the marker; and
a display designed to depict information relating to the ability to withstand power injection, the information comprising alphabetic characters,
wherein the external detection device is designed to detect and process the ultrasound signal reflection by the marker and to display the information relating to the ability to withstand power injection.

6. The identification system of claim 5, wherein the alphabetic characters form a written message.

7. The identification system of claim 5, wherein the marker comprises a plurality of markers spaced along a longitudinal length of the catheter.

8. The identification system of claim 7, wherein the plurality of markers are arranged in a specified pattern relating to the at least one attribute of the access port.

9. The identification system of claim 8, wherein the plurality of markers are arranged in a bar code.

10. The identification system of claim 9, wherein the plurality of markers are non-uniformly spaced.

11. The identification system as defined in claim 2, wherein the first marker is configured to indicate an implanted location of the access port.

12. The identification system of claim 2, wherein the first marker is configured to assist in determining an orientation of the access port.

13. The identification system of claim 1, wherein the information regarding the at least one attribute of the access port to be depicted on the display is different from a depiction of the predetermined pattern itself.

14. The identification system of claim 1, wherein the information regarding the at least one attribute of the access port to be depicted on the display comprises words describing the at least one attribute, the words determined based on how the detection device interprets the predetermined pattern.

* * * * *